United States Patent [19]

Murch

[11] 3,943,197

[45] Mar. 9, 1976

[54] ALKOXY DERIVATIVES OF THE ADDUCT FROM PHOSPHOROUS PENTACHLORIDE AND HEXAMETHYLPHOSPHORAMIDE

[75] Inventor: Robert M. Murch, Ashton, Md.

[73] Assignee: The United States of America as represented by the Secretary of the Navy, Washington, D.C.

[22] Filed: June 19, 1974

[21] Appl. No.: 480,912

[52] U.S. Cl.......... 260/926; 260/45.7 P; 260/551 P
[51] Int. Cl.$^2$............................................ C07F 9/02
[58] Field of Search............................ 260/926, 920

[56] References Cited
OTHER PUBLICATIONS

Kosolapoff, "Organophosphorus Compound", J. Wiley & Son, Inc., New York, (1950), p. 226.

*Primary Examiner*—Anton H. Sutto
*Attorney, Agent, or Firm*—R. S. Sciascia; Arthur L. Branning; Thomas McDonnell

[57] ABSTRACT

The adduct of phosphorous pentachloride ($PCl_5$) and hexamethylphosphoramide (($Me_2N)_3PO$) and alkoxy derivatives thereof useful for enhancing the fire retardancy of polyesters and a method of enhancing the fire retardancy of general purpose polyester resins through the combination therewith of the aforedescribed alkoxy derivative.

4 Claims, No Drawings

ALKOXY DERIVATIVES OF THE ADDUCT FROM PHOSPHOROUS PENTACHLORIDE AND HEXAMETHYLPHOSPHORAMIDE

BACKGROUND OF THE INVENTION

General purpose polyester resins can be used for most types of molding and laminating. By polyester is meant the polycondensation product of dicarboxylic acids with dihydroxy alcohols in contradistinction to materials known as alkyds. These polyester compounds may be modified by mono-carboxylic acids, monohydroxy alcohols and small amounts of polycarboxylic acids or polyhydroxy alcohols. Such compounds have a wide range of properties and a particular resin may have properties that may make it suitable for one purpose but unsuitable for another. For example, high viscosity resins are useful in vertical layup, where low viscosity resins, however, would be required when rapid penetration was desirable.

The wide range of properties possible with polyester resins leads to a variety of applications. They can be used as the primary polymer in fiber reinforced laminates and as the binder in composites containing a variety of inert fillers. Castings, potting compounds, cements, sealing and patching compounds, rigid and flexible coatings and adhesives can be based on polyester resins. As distinct from saturated polyesters, the resins contain olefins which produce the highly cross-linked structure generally known as a thermoset polymer.

While the uses of general purpose polyester resins continue to steadily grow, such resins suffer from the drawback that due to their high hydrogen and carbon content they continue to burn fairly readily once ignited. Since much concern has been generated by consumers to reduce the flammability of products such as flammable fabrics, manufacturers have had to find ways to reduce the flammability of polyesters and polyester resins.

The flammability of polyester resins can be reduced in several ways. These include chemical modification of one or more of the resin components, addition of organic fire retardants or addition of inorganic fillers and fire retardants.

A common chemical modification is replacing the diacid with a diacid containing halogen. Tetrachlorophthalic and tetrabromophthalic anhydrides are commonly used. One of the most widely used anhydrides is chlorendic anhydride, made by the Diels-Alder addition of hexachlorocyclopentadiene to maleic acid.

Other common polymer modifications include post bromination of the resin and the use of brominated diols. Halogenated styrene has been used and there are numerous known examples of the attachment of phosphorus-containing moieties to the diols, diacids or cross-linking olefins.

Two main types of organic compounds are commonly used as soluble, non-reactive additives. Halogen-containing aliphatic or aromatic compounds are commonly cited. Phosphorus compounds such as triethylphosphate are also well known in the art. Currently the combination of the two, i.e., tris-$\beta$-chloroethylphosphate or 2,3-dibromopropyl phosphate have been widely used. In all of these cases the amount of additive is limited by possible plasticizing effects. Even small amounts of organometallics, examples being ferocene or ferocene derivatives have been recommended as desirable additives.

A number of inorganic additives are commonly added. Of course, glass fibers or cloth are used to increase the strength of the resin, but this may or may not help the flammability. The use of inert fillers such as calcium carbonate, magnesium oxide, etc. usually help the flammability characteristics in a minor way. The addition of hydrated salts and oxides, aluminatrihydrate being the most widely used, are effective by acting as a heat sink that slows down the energy transfer to the polymer. Antimony oxide is used, usually in conjunction with halogens, the latter may be incorporated as part of the resin or as a separate additive. Another commonly used inorganic additive is zinc borate.

Thus, while the techniques used to reduce the flammability of polyester resins do so to some extent, all suffer from some drawback.

SUMMARY OF THE INVENTION

It is therefore an object of the present invention to provide general purpose polyester resins having low flammability characteristics.

Another object of the invention is to provide additives which enhance the fire retardancy of polyester resins.

Another object of the invention is to provide a method for enhancing the fire retardancy of polyester resins.

And another object of the invention is to provide fire retardant additives for general purpose polyester resins which are cheap and readily available.

Yet another object of the invention is to provide fire retardant additives for general purpose polyester resins which give minimum interference with the properties of the resin.

And yet another object of this invention is to provide a general purpose polyester resin having a low flammability without having a reduced outside durability.

These and other objects are achieved by reacting the adduct of phosphorous pentachloride and hexamethylphosphoramide with an alcohol thereby producing an alkoxy derivative capable of enhancing the fire retardancy of polyester resins.

DETAILED DESCRIPTION

In accordance with the novel aspects of the invention, general purpose polyester resins are rendered fire retardant by adding thereto an alkoxy derivative. By "fire retardant" is meant that the resin is resistant to flame after the igniting flame has been removed. In other words the fire retardant polyester resins will not support combustion by itself. When in contact with an open flame, however, it may become charred.

Generally, polyesters are formed by the reaction of a dibasic acid with a polyhydric alcohol, such as, ethylene glycol. If either the acid or the alcohol is unsaturated, an unsaturated polyester is obtained that is capable of subsequent cross-linking either directly to similar unsaturated double bonds in adjacent polyester chains of the same structure or through an unsaturated double bond in a monomer such as styrene. An example of the latter is poly (propylene maleate/phthalate) in styrene which has long been used as a guide to compare with other more complex polyester resins. It is produced by reacting 2 moles of propylene glycol, 1 mole of phthalic anhydride, 1 mole of maleic anhydride, hydroquinone equally 0.2 percent by volume of the final solution, and monomer styrene equaling 35 percent by volume of the final solution. In the examples hereinafter presented poly (propylene maleate/phthalate) in styrene was used to test the ability of the additive to render polyester resins fire retardant.

The fire retardancy enhancing additives of the invention are best produced by mixing at room temperature for at least about 10 minutes but preferably for about 20 minutes in a mole ratio of 1:1 phosphorous pentachloride ($PCl_5$) and hexamethylphosphoramide ($Me_2N)_3PO$ in benzene in an amount at least sufficient to dissolve reactants. This reaction forms the adduct of $PCl_5$ and $(Me_2N)_3PO$ which has utility as a fire retardant but due to an adverse side reaction when mixed with a polyester, this adduct is less important than its alkoxy derivative for polyester systems.

At the completion of the reaction which is evidenced by the reaction mixture becoming clear, the mixture is allowed to cool to 20° to 30° centigrade below the product reflux temperature of approximately 80°C. The purpose of this step is to prevent the forthcoming adduct-alcohol reaction from becoming uncontrolled. Such a condition would be evidenced by a markedly turbulent reaction mixture. The adduct-alcohol reaction is carried out by mixing together the aforementioned reaction mixture with an alcohol in an alcohol-to-$PCl_5$ mole ratio of 3:1 and with pyridine in a pyridine-to-$PCl_5$ mole ratio of 3:1. Isolation of the product is achieved by filtering the by-product pyridine hydrochloride and then by evaporating the solvent.

Alcohols found useful are methanol, ethanol, β-chloroethanol, 3,3,3-trichloro-propanol, 2,3-dibromo-propanol, 1,3-dichloro-2-propanol, and 2,2,2-trichloroethanol. It is expected a good many of the alcohols would yield similar results.

The amount of the additives of this invention which is added in order to enhance the fire retardancy of general purpose polyesters is from about 5 to 20 weight percent of the total mixture. Inclusion of the additive is made after the polyester is prepared, but before it is cured.

As stated previously, polyester resins may be cross-linked either directly or through an unsaturated monomer. When cross-linked quite often a catalyst is used. Among the catalysts useful for such purposes are the peroxides. Some decompose at high temperatures, therefore, the choice of an appropriate catalyst depends on the intended molding or curing temperature. Benzoyl peroxide starts to decompose at 50°C and is therefore used for resins which are cured at high temperatures. Methylethyl ketone peroxide is used at lower temperatures especially with a cobalt accelerator such as cobalt naphthenate. Table I taken from *Polyesters and their Applications*, Bjorksten Research Laboratories, Inc., Reinhold Publishing Corp., New York, 1956, p. 49, lists commonly used peroxide catalysts.

TABLE I

| Trade Name | Composition | Physical form | Peroxide assay % | Supplier* |
|---|---|---|---|---|
| — | Benzoyl peroxide | granules | 96 | 2 |
| — | Benzoyl peroxide | fine granules | 96 | 2 |
| — | Benzoyl peroxide purified | fine crystals | 96 | 2 |
| LUCIDOL | Benzoyl peroxide | fine crystals | 96 | 1 |
| LUPERCO ATC | Benzoyl peroxide compounded with tricresyl phosphate | thick paste | 50 | 1 |
| CADOX BTP | Benzoyl peroxide compounded with tricresyl phosphate | thick paste | 50 | 2 |
| LUPERCO CDB | 2,4-Dichlorobenzoyl peroxide compounded with dibutyl phthalate | thick paste | 50 | 1 |
| LUPERSOL DDM | Methylethyl ketone peroxide in dimethyl phthalate | liquid | 60 | 1 |
| CADON MDP | Methylethyl ketone peroxide in dimethyl phthalate | liquid | 60 | 2 |
| — | Cyclohexanone peroxide (mixed ketone peroxides) | granules | 96 | 1 |
| LUPERCO JDB | Cyclohexanone peroxide compounded with dibutyl phthalate | thick paste | 50 | 1 |
| — | Cumene hydroperoxide | liquid | 73 (as hydroperoxide) | 3 |

*Supplier:
(1) Lucidol Div., Wallace and Tiernan, Inc., Buffalo, N.Y.
(2) McKesson and Robbins, Inc., Chem. Div., N.Y. (distributors for Cadet Chem. Corp., Buffalo, N.Y.)
(3) Hercules Powder Co., Nav. Stores Dept., Wilmington, Del.

Other peroxide catalysts mentioned in the polyester patent literature are bis(para-bromobenzoyl) peroxide, bis(phthalyl) peroxide, bis(para-chlorobenzoyl) peroxide, bis(succinyl) peroxide, acetylbenzoyl peroxide, bis(chloroacetyl) peroxide, bis(acetyl) peroxide, tertiary-butyl perbenzoate, tertiary-butyl hydroperoxide, bis(dichlorobenzoyl) peroxide, oxonide, peracetic acid, perbenzoic acid, benzoyl peracetate, and peroxycarbonates such as ethyl peroxidicarbonate.

Accelerators other than cobalt naphthenate may be used as well. Among these are the vanadium accelerators and dimethylp-toluidine. Other catalysts such as dimethylaniline may be used as well. When using these accelerators and catalysts to promote cross-linking the polyester resin, it may be beneficial to heat the resin. The temperature at which to heat the resin is dependent upon the curing system being empolyed and is well within the skill of the art.

In order to more fully illustrate the invention the following examples are presented. The purpose of the examples is to illustrate the fire retardancy characteristics obtained by adding the alkoxy derivative to a general purpose polyester resin that is often used to make comparisons with other complex polyester resins. Therefore, the use herein of the general purpose polyester resin is meant to be illustrative and not a limitation as to the scope of the invention.

EXAMPLE 1

Phosphorous pentachloride ($PCl_5$), 20.9 g., was slurried in 150 ml of benzene and hexamethylphosphoramide, $[(CH_3)_2N]_3PO$, 17.9 g., was added slowly. This caused the reaction mixture to heat from 23°C to 45°C. After completing the addition, the reaction mixture was heated until a clear solution was formed and then held at 80°C for one and one-half hours. The reaction mixture was cooled and ethanol, 13.8 g., was added slowly. During this addition the temperature rose from 53°C to 70°C. Evolution of HCl could be observed during this addition and during the subsequent 2 hour heating period at 80°C. The product was obtained by removing the solvent and volatile byproducts. The product, 23.2 g., was a light straw-colored liquid with an acid number of 3.56 meq/g. This represents a replacement of about 80 percent of the halogen with ethoxy groups.

EXAMPLE 2

$PCl_5$, 20.9 g. and $[(CH_3)_2N]_3PO$, 17.9 g., were combined in benzene and after the exothermic reaction was complete, 2,2,2-trichloroethanol, 44.85 g., was added slowly. This mixture was heated to the reflux temperature and held for 11 hours at which time the evolution of HCl could no longer be detected. The product, isolated by distilling the solvent and the volatile by-product, weighed 55 g.

EXAMPLE 3

The reaction of $PCl_5$, 20.9 g., and $[(CH_3)_2N]_3PO$, 17.9 g., was conducted in benzene as before, then 3,3-dichloro-2-propanol, 38.7 g., was added and the reaction mixture held at the reflux temperature for two hours. The product was isolated as the residue after distilling to 120°C at 0.5 mm Hg.

EXAMPLE 4

The same reaction with 2,3-dibromopropanol, 65.4 g., produced a viscous brown liquid as the residue upon distilling to 110°C at 0.1 mm Hg. This material had an acid number of 1.24 meq/g.

EXAMPLE 5

A resin containing 90 parts of a general purpose polyester (GR-941-Marco Chemical Division of W. R. Grace and Co.) and 10 parts of the additive described in Example 1 was cured by the addition of .02 parts of cobalt naphthenate and 0.1 part of methylethyl ketone peroxide and then by heating at 70°C for four hours. This resin had a Barcol hardness of 40 and an oxygen index of 0.236.

EXAMPLE 6

Using the technique described in Example 5 and the additive from Example II, a resin with a Barcol hardness of 40 and an oxygen index of 0.260 was obtained.

EXAMPLE 7

Using the technique described in Example 5 and the additive from Example 3 a resin with a Barcol hardness of 38 and an oxygen index of 0.236 was produced.

EXAMPLE 8

Using the technique described in Example 5 and the additive described in Example 4 resin with a Barcol hardness of 41 and an oxygen index of 0.248 was produced.

Example 1 illustrates the manner in which the adduct of phosphorous pentachloride and hexamethylphosphoramide is produced, and further illustrates the production of an alkoxy derivative encompassed by this invention. Examples 2–4 illustrate the production of three different alkoxy derivatives by reacting the adduct of Example 1 with various alcohols. Examples 5–8 are illustrative of the use of alkoxy derivatives used as fire retardant additives to the polyester resins. In the examples the oxygen index was obtained by using the method disclosed ASTM D-2863-70. By "oxygen index" is meant the minimum oxygen concentration, expressed in volume percent, in a mixture of oxygen and nitrogen that will just support combustion of a material under the conditions of the method. Accordingly, a material having high oxygen index requires more oxygen to support combustion, and is therefore more fire retardant than are having a low oxygen index. In each of the examples the additive enhanced the fire retardation capabilities of the polyester resin.

The polyester resin used in the examples has an oxygen index of 0.18. It is apparent that the use of the additive of the invention significantly increases the fire retardancy of the resin.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A compound having the formula: $(RO)_3PCl_2\cdot(Me_2N)_3PO$, wherein R = $ClCH_2CH_2$, $Cl_3CCH_2$, $Cl_3CCH_2CH_2$ $(ClCH_2)_2CH$, $CH_2BrCHBrCH_2$, $CH_3$ and $C_2H_5$.

2. The compound of claim 1 wherein R = $CH_3$ and $C_2H_5$.

3. The compound of claim 1 wherein R = $ClCH_2CH_2$ and $Cl_3CCH_2$.

4. The compound of claim 1 wherein R = $(ClCH_2)_2CH$, $Cl_3CCH_2CH_2$, and $CH_2BrCHBrCH_2$.

* * * * *